United States Patent
Ritz et al.

(10) Patent No.: US 8,646,312 B2
(45) Date of Patent: Feb. 11, 2014

(54) METHOD AND SYSTEM FOR MEASURING RON AND MON VALUES FOR LIGHT DISTILLATES

(75) Inventors: G. Patrick Ritz, Irvine, CA (US); Didier Pigeon, Ifs (FR)

(73) Assignee: Petroleum Analyzer Company, LP, Houston, TX (US)

( * ) Notice: Subject to any disclaimer, the term of this patent is extended or adjusted under 35 U.S.C. 154(b) by 1709 days.

(21) Appl. No.: 11/949,610

(22) Filed: Dec. 3, 2007

(65) Prior Publication Data
US 2008/0213914 A1 Sep. 4, 2008

Related U.S. Application Data

(60) Provisional application No. 60/868,275, filed on Dec. 1, 2006.

(51) Int. Cl.
*G01N 33/22* (2006.01)

(52) U.S. Cl.
USPC ....... 73/35.02; 73/35.01; 73/35.03; 73/35.04; 73/35.05; 73/35.06; 702/11; 702/12; 702/22

(58) Field of Classification Search
None
See application file for complete search history.

(56) References Cited

U.S. PATENT DOCUMENTS

| | | | |
|---|---|---|---|
| 3,463,613 A * | 8/1969 | Fenske et al. | 436/55 |
| 5,633,798 A * | 5/1997 | Kopp | 701/111 |
| 2005/0256352 A1* | 11/2005 | Clark et al. | 585/14 |
| 2007/0246005 A1 | 10/2007 | Sobotowski | |

FOREIGN PATENT DOCUMENTS

| | | |
|---|---|---|
| EP | 0 737 862 A | 10/1996 |
| WO | WO 2006/136349 | 12/2006 |

OTHER PUBLICATIONS

Bowden et al., Octane-Cetane Relationship, Mar. 1974, pp. 1-16.*
Olivieri, On a versatile second-order multivariate calibration method based on partial least-squares and residual bilinearization: Second-order advantage and precision properties, J. Chemometrics 2005; 19: pp. 253-265.*
Bradley et al., Engine autoigntion: Therelationship between octane numbers and autoignition delay times, Combustion and Flame 147 (2006), pp. 171-184.*
ASTM Standard D 2699, 2004, "Standard Test Method for Research Octane Number of Spark-Ignition Engine Fuel," ASTM International, West Conshohocken, PA, 2004, www.astm.org.*
Determination of Ignition Delay and Derived CETANE No. (DCN) of Diesel Oils by Combustion in a Constant Volume Chamber, ASTM Designation, ASTM International, US, vol. D6890-4, May 2004.
Hashimoto et al. "Evaluation of ignition quality of lpg with cetane number improver," SAE Technical Paper Series 2002-01-0870, 2002, XP002473484.
PCT ISR and Written Opinion to PCT Counterpart, Mar. 12, 2007.
PCT ISR and Written Opinion of related PCT counterpart, Mar. 12, 2007.
U.S. Appl. No. 11/949,600, filed Dec. 3, 2007—related case.
R.D. Matthews, Mechanical Engineer's Handbook: Energy and Power, vol. 4, 3rd ed., Chpt. 27, Feb. 16, 2006, John Wiley & Sons, Inc. XP002473653.
Ryan III & Matheaus, "Fuel requirements for HCCI engine operation," SAE Paper 2003-01-1813, 2003, XP002473652.

\* cited by examiner

*Primary Examiner* — Paul Hyun
*Assistant Examiner* — Robert Eom
(74) *Attorney, Agent, or Firm* — Gunn, Lee & Cave, P.C.

(57) ABSTRACT

A method and a system is disclosed for determining RON and/or MON values from constant volume combustion chamber apparatuses capable of producing pressure versus time combustion profiles having a fast combustion region and a slow combustion region, where data from the two regions is used to compute RON and/or MON values for light distillate fluid samples using a series expansion equation.

11 Claims, 2 Drawing Sheets

METHOD AND SYSTEM FOR MEASURING RON AND MON VALUES FOR LIGHT DISTILLATES

RELATED APPLICATIONS

The present application claims priority to U.S. Provisional Patent Application Ser. No. 60/868,275 filed 1 Dec. 2006 (Dec. 1, 2006).

BACKGROUND OF THE INVENTION

1. Field of the Invention

The present invention relates to a method and a system of measuring RON and/or MON values of lower boiling point hydrocarbon fluids and/or fuels.

More particularly, the present invention relates to a method and a system of measuring RON and/or MON values of lower boiling point hydrocarbon fluids and/or fuels, where the method includes combusting a sample of a lower boiling point hydrocarbon fluid and/or fuel in a constant volume combustion chamber (CVCC) under conditions to produce combustion data of pressure versus time or a combustion pressure versus time profile, selecting one data point or a plurality of data points from the data and deriving a RON and/or MON value using a series expansion about the selected points.

2. Description of the Related Art

Current methods and systems for measuring RON and/or MON values are based either on engine data or are based on data from a constant volume combustion chamber. The methods and systems utilizing constant volume combustion chamber apparatuses determine RON and/or MON values from an equation that uses a single point from the of pressure versus time combustion data that corresponds to a given change in chamber pressure after injection of a fuel sample. These methods are wrought with uncertainty for fuels having different amount of faster burning fuel components and using apparatuses that a capable of differentiating between faster and slower burning fuel components.

Thus, there is a need in the art for methods and systems for determining RON and/or MON values from constant volume combustion chamber apparatuses, especially in apparatuses capable of differentiating between faster and slower burning fluid components, where the methods and systems utilize data a pressure versus time profile in a series expansion about selected data points from the curve to derive improved RON and/or MON values for lower boiling point hydrocarbon fluids and/or fuels.

SUMMARY OF THE INVENTION

The present invention provides a system and method capable of determining RON and/or MON values from a pressure v. time combustion profile of a lower boiling point hydrocarbon fluid and/or fuel, where the data or profile includes a single combustion region or multiple combustion regions.

The present invention also provides a system and method capable of determining RON and/or MON values from a pressure v. time combustion profile of a lower boiling point hydrocarbon fluid/fuel, where the data or profile includes a first region, an A region or early ignition delay region, and a second region, a B region or late ignition delay region. The A region represents fluid/fuel components having a first combustion rate and the B region represents fluid/fuel components having a second combustion rate, where the first combustion rate is faster than the second combustion rate.

The present invention provides a system for computing RON and/or MON values of lower boiling point hydrocarbon fluids and/or fuels including a constant volume combustion chamber (CVCC) subsystem having a pressure sensor, a source of an oxidizing agent, a lower boiling point hydrocarbon fluid/fuel source, a pressurizing means and a heating means. The system also includes an analyzing subsystem adapted to accumulate data during combustion of a sample in the CVCC subsystem to produce a pressure versus time data or a pressure versus time data profile, and to compute derived RON and/or MON values from at least one data point selected the data profile as an independent variable in a power series expansion about the selected data points.

The present invention provides a system for computing RON and/or MON values of lower boiling point hydrocarbon fluids and/or fuels including a constant volume combustion chamber (CVCC) subsystem having a pressure sensor, a source of an oxidizing agent, a lower boiling point hydrocarbon fluid/fuel source, a pressurizing means and a heating means. For combustion data profiles that include two combustion regions, an A region and a B region, the system also includes an analyzing subsystem adapted to accumulate data during combustion of a sample in the CVCC subsystem to produce pressure versus time data profile, and to compute a derived RON and/or MON value from at least one point selected from either the A region or the B region as an independent variable in a power series expansion about the selected points.

The present invention provides a system for computing RON and/or MON values of lower boiling point hydrocarbon fluids and/or fuels including a constant volume combustion chamber (CVCC) subsystem having a pressure sensor, a source of an oxidizing agent, a lower boiling point hydrocarbon fluid/fuel source, a pressurizing means and a heating means. For combustion data profiles that include two combustion regions, an A region and a B region, the system also includes an analyzing subsystem adapted to accumulate data during combustion of a sample in the CVCC subsystem to produce pressure versus time data profile, and to compute a derived RON and/or MON value from at least one point selected from at least one data point selected from the A region and at least one data point selected from the B region as independent variables in a power series expansion about the selected points.

The present invention also provides a method including the step of combusting a sample of a lower boiling point hydrocarbon fluid and/or fuel in a constant volume combustion chamber (CVCC) apparatus having a pressure sensor to produce combustion pressure versus time data, plottable as a pressure versus time profile. The method also includes the step of selecting at least one data point from the profile as an independent variable for a power series expansion about the selected point or points. The method also includes the step of computing a derived RON and/or MON value utilizing the selected point or points as independent variables in a power series expansion about the selected points, where the derived RON and/or MON value has a greater accuracy than a RON and/or MON value calculated from a non-power series expansion using only a specific point from the same data. The method can also include the step of calibrating coefficients of the expansion equation using sample with known RON and/or MON values.

The present invention also provides a method including the step of combusting a sample of a lower boiling point hydrocarbon fluid and/or fuel in a constant volume combustion chamber (CVCC) apparatus having a pressure sensor to produce combustion pressure versus time data, plottable as a pressure versus time profile. For data profiles that include a first region, the A region, and a second region, the B region, the method also includes the step of selecting at least one data point from the profile as the independent variable for a power series expansion about the selected point or points. The selected points can include one or more points from either the first region of the profile corresponding to ignition of faster burning components of the fluid/fuel or the second region of the profile corresponding to ignition of slower burning components of the fluid/fuel or both. The method also includes the step of computing a derived RON and/or MON value utilizing the selected point or points as independent variables in a power series expansion about the selected points, where the derived RON and/or MON value has a greater accuracy than a RON and/or MON value calculated from a non-power series expansion using only a specific point from the same data. The method can also include the step of calibrating coefficients of the expansion equation using sample with known RON and/or MON values.

The present invention also provides a method including the step of combusting a sample of a lower boiling point hydrocarbon fluid and/or fuel in a constant volume combustion chamber (CVCC) apparatus having a pressure sensor to produce combustion pressure versus time data, plottable as a pressure versus time profile. For data profiles that include a first region, the A region, and a second region, the B region, the method also includes the step of selecting at least one point from the A region and at least one point from the B region. The method also includes the step of deriving a RON and/or MON value from an equation using the least one point from the A region and the at least one point from the B region as independent variables in a power series expansion about the point to compute a derived RON and/or MON value that is closer to an actual RON and/or MON value of the sample as compared to computing a RON and/or MON value from a non-power series expansion using only a specific point from the same data. The method can also include the step of calibrating coefficients of the expansion equation using sample with known RON and/or MON values.

The represent invention also provide a method for determining coefficients of a series expansion equation for calculating derived RON and/or MON values comprising the step of combusting a sample having a known RON and/or MON value in a constant volume combustion chamber apparatus under controlled conditions to obtain pressure versus time combustion data. Next, at least one point from the profile is selected and a derived RON and/or MON value using the series expansion equation about the selected points with a set of initial coefficients is computed or calculated. Next, the coefficients of the series expansion equation are adjusted so that a difference between the RON and/or MON and the derived RON and/or MON value is minimized.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that a new method can be formulated for determining derived RON and/or MON values of lower boiling point hydrocarbon fluids and/or fuels from combustion data derived from a constant volume combustion chamber (CVCC) apparatus. The inventor has found that superior derived RON and/or MON values can be calculated using a series expansion equation, expanded about one data point or a plurality of data points from a pressure versus time data collected when a lower boiling point hydrocarbon fluid and/or fuel sample is burned in the CVCC apparatus. The inventor has found that superior RON and/or MON number values can be obtained using the CVCC capable of yielding a pressure/time profile including multiple combustion regions. For example, certain pressure/time profiles include an A region and a B region produce, where the A region represents fuel components with shorter (early) ignition delay times (faster burning components) and the B region represents fuel components with longer (later) ignition delay times (slower burning components). The inventor has found RON and/or MON number calculations using at least one data point selected from each combustion region as the independent variables yield superior derived RON and/or MON number values than calculations based on only a single, specific pressure/time data point. For example, profiles having an A region and a B region, RON and/or MON number values derived from equations using at least one point from the A region and at least one data point selected from the B region yield superior derived RON and/or MON number values than calculations based on only a single, specific pressure/time data point.

The present invention broadly relates to a system for determining derived RON and/or MON values for unknown lower boiling point hydrocarbon fluid and/or fuel samples. The system includes a combustion subsystem comprising a constant volume combustion chamber (CVCC) apparatus for obtaining pressure versus time data from the combustion of an unknown lower boiling point hydrocarbon fluid and/or fuel sample. The system also includes an analzying subsystem for selecting at least one data point from the A region and at least one data point from the B region and calculating RON and/or MON value from a equation relating the RON and/or MON value to the value of the selected points.

The present invention also broadly relates to a method including the step of combusting a sample of a lower boiling point hydrocarbon fluid and/or fuel in a constant volume combustion chamber (CVCC) apparatus having a pressure sensor to produce combustion pressure versus time data, plottable as a pressure versus time profile. The method also includes the step of selecting at least one data point from a first region of the profile corresponding to ignition of faster burning components of the fluid/fuel and at least one data point from a second region of the profile corresponding to ignition of slower burning components of the fluid/fuel. The method also includes the step of computing derived RON and/or MON values utilizing the at least one data point from the first region and the at least one data point from the second region as independent variables.

Suitable hydrocarbon fluids and/or fuels includes, without limitation, any hydrocarbon fluid or fuel that has a lower boiling point in the context of refined hydrocarbons derived from crude oil or bio-material fluids or fuels or synthetic fluids or fuels with boiling points in the range of lower boiling point refined hydrocarbons, or mixtures or combinations thereof. Naphthas are refined or partly refined light distillates with an approximate boiling point range of 27 degrees to 221 degrees Centigrade. Blended further or mixed with other materials, they make high-grade motor gasoline or jet fuel. Also, used as solvents, petrochemical feedstocks, or as raw materials for the production of town gas. Non-limiting exemplary examples of such fluids include gasolines, The system and method of this invention utilize data derived from a constant volume combustion chamber (CVCC) apparatus to compute derived RON and/or MON values for a lower boiling point hydrocarbon fluid/fuel, where a lower boiling point hydrocarbon fluid/fuel sample is combusted at an elevated temperature and pressure. The sample is injected into the CVCC apparatus at a predetermined pressure and temperature. After injection, a pressure in the chamber is measured as a function of time after injection until combustion is complete. In older devices, one data point from the pressure/time data representing an ignition delay was selected to be used in an equation to compute or calculate a derived RON and/or MON that would correspond to RON and/or MON measured using a special internal combustion engine. However, with the advent of new fuel mixtures, the derived RON and/or MON values have shown mark deviations from the actual RON and/or MON values. In new CVCC apparatuses, the pressure/time profile can have two distinct regions, while in other data, the profile can just including one region or the two regions can be such that the early burning components curve are a mere shoulder on the late burning components curve. The first region, sometimes referred to herein as the A region, represents fluid/fuel components that have a shorter ignition delay (start burning earlier), and the second region, sometimes referred to herein as the B region, represents fluid/fuel components that have a longer ignition delay (start burning later). Because fluids/fuels generally give rise to a two region pressure/time profile when tested in a CVCC, the derived RON and/or MON values show considerable and inconsistent disagreement with their corresponding actual RON and/or MON values. The present method significantly reduces these variances, by using at least one data point from each region of the pressure/time profile in an series expansion equation to generate derived RON and/or MON values having smaller variances from their corresponding actual RON and/or MON values, where the expansion is relative to the selected data points—the selected data point are the independent variables in the equation.

Figure 1:
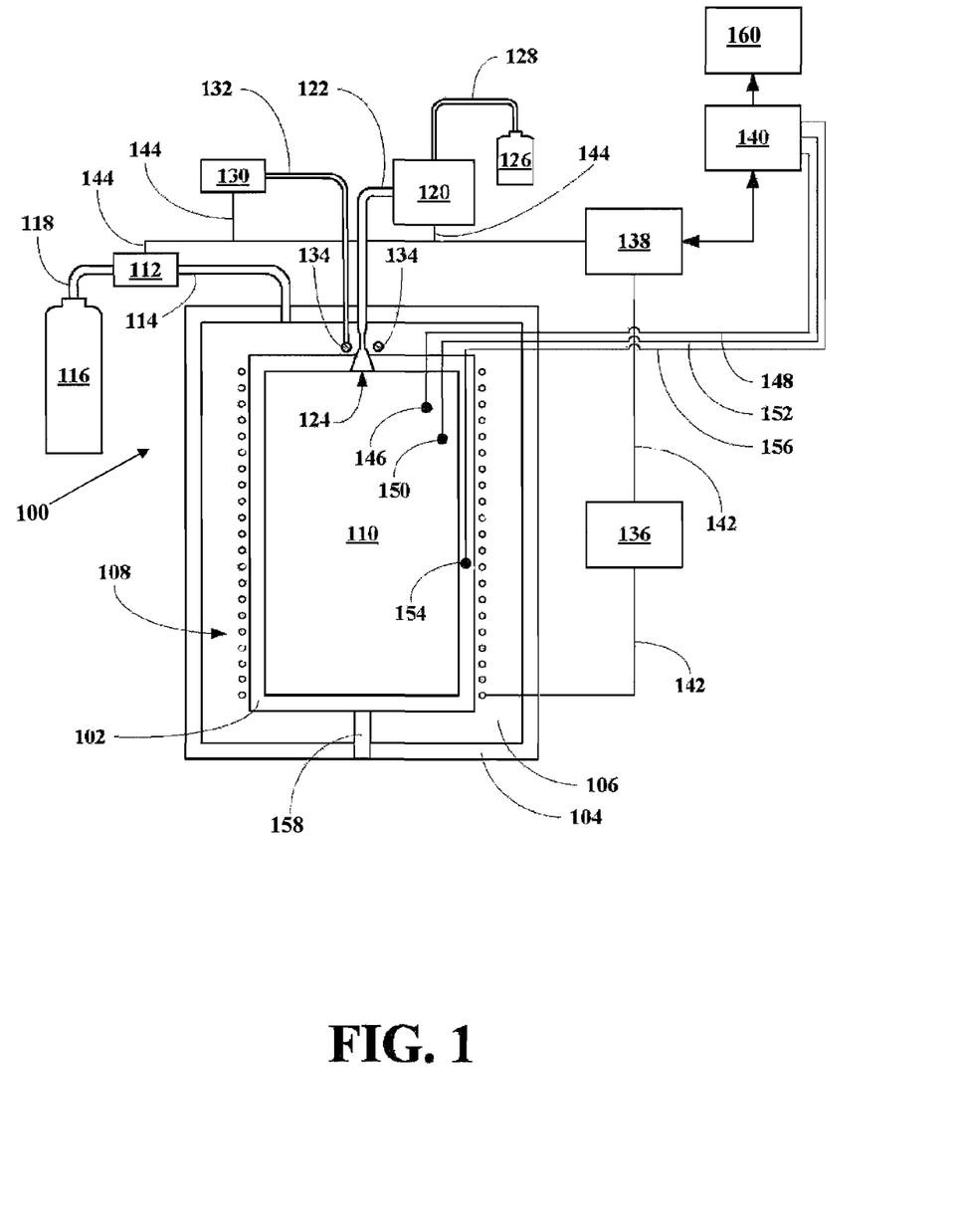
FIG. 1 depicts a constant volume combustion chamber (CVCC) apparatus for measuring time/pressure profiles for samples to be combusted.

Referring now to FIG. 1, a constant volume combustion chamber (CVCC) apparatus for measuring pressure versus time data or data profiles of fluid samples for uses in the methods of this invention, generally 1, is shown. Using this type of CVCC apparatus, samples can be combusted in a controlled manner to yield pressure/time data from which at least one point from each region, the A region and the B region, can be selected and used in a series expansion equation with respect to the selected values to derive improved derived RON and/or MON values for the fluid samples.

The apparatus 100 includes combustion chamber 102 having a fixed capacity or volume. The combustion chamber 102 is surrounded by an outside container 104 adapted to accommodate a whole of the combustion chamber 102 in a sealed condition. Between the outer container 104 and the chamber 102 is a thermal insulator 106 encasing a heating means 108 adapted to heat an interior 110 of the combustion chamber 102 to a predetermined temperature. The apparatus 100 also includes a pressure regulator 112 for pressurizing the interior 110 of the combustion chamber 102 to a predetermined pressure via compressed air feed conduit 114. The pressure regulator 112 is connected to a source of compressed air 116, which is used to adjust the pressure in the interior 110 to the predetermined pressure, via a compressed air supply conduit 118. The apparatus 100 also includes a high pressure injection system 120 for injecting a sample fuel into the combustion chamber 102 via a sample feed tube 122 through a nozzle 124. The sample is supplied to the injection system 120 from a sample container 126 via a sample supply conduit 128 under pressure sufficient to. The apparatus 100 can optionally include a cooler pump 130 containing a coolant and adapted to circulate the coolant via a conduit 132 and ports 134 in the insulator 106 to cool the nozzle 124. The apparatus 100 also includes a power supply 136, a controller 138 and an analyzer 140, where the power supply 136 supplies power to the heater 108 and the controller 138 via power cables 142. The controller 138 is connected to the injector 120, the pressure regulator 112 and the coolant pump 130 via control cables 144 and coolant pump 130 via control cables 144 and adapted to supply power and control on these devices so that a sample can be combusted in the chamber 102 under controlled condition. The analyzer 140 includes a pressure sensor 146 located in the interior 110 or on an interior surface of the chamber 102 and connected to the analyzer 140 by sensor cable 148. The analyzer 140 is adapted to receive pressure data from the sensor 146 so that a time versus pressure profile can be recorded for each sample injected into the combustion chamber 102. The analyzer 140 also includes a first temperature sensor 150 located in the interior 110 of the chamber 102 and connected to the analyzer 140 by a first temperature sensor cable 152, and a second temperature sensor 154 located in the wall of the chamber 102 and connected to the analyzer 140 by a second temperature sensor cable 156. The analyzer 140 is adapted to receive temperature data from the sensors 150 and 154 so that a temperature of the combustion in the combustion chamber 102 can be controlled. The apparatus 100 also includes an exhaust port 150. The apparatus 100 can be includes an output device 160 such as a display device, a graphing device, a printer or a combination of these types of devices. Post 158 maintains the position of the combustion chamber 102 with respect to outer container 104.

Once a samples has been combusted in an apparatus of FIG. 1 and its pressure/time data profile obtained, a plurality of data points from the profile are selected as independent variables in an equation comprising a power series expansion around the selected points to compute derived RON and/or MON values having smaller variances with respect to their corresponding actual RON and/or MON values. In certain embodiments, the plurality of data points include one data point from the A region (early burning components) and one data point from the B region (later burning components). The coefficients in the series expansion are determined by fitting the equation to samples with known actual RON and/or MON values, i.e., the equation is calibrated or tuned using standard or reference fluids/fuels having known RON and/or MON values.

In one embodiment, a derived RON is calculated from second order equation (I):

$$RON = C_{1a} * ID_1 + C_{2a} * ID_2 + C_{1b} * (ID_1)^2 + C_{2b} * (ID_2)^2 + I \qquad (I)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$ are coefficients and I is the intercept, where the coefficients obtained from solving equation (I) for a set of standard or reference samples with known RON value. In equation (I), the coefficients of $ID_1$ or $ID_2$ can be set to zero so that the derived RON values are calculated based on a power series expansion about a single ID measurement.

In one embodiment, a derived RON is calculated from second order equation (II):

$$RON = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \quad (II)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$, $C_{ra}$, and $C_{rb}$ are coefficients and I is the intercept, where the coefficients are obtained from solving equation (II) for a set of standard or reference samples with known RON values. In equation (II), the coefficients of any of the terms can be set to zero so that the derived RON values are calculated based on a power series expansion about a single ID or a single ratio of selected data points. In certain embodiment, the coefficient $C_{rd}$ is set equal to zero. It should be recognized that the value of the coefficients will change depending on the points selected.

In one embodiment, a derived RON is calculated from second order equation (III):

$$RON = C_{ra}ID_1/ID_2 + C_{rb}(ID_1/ID_2)^2 + I \quad (III)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{ra}$ and $C_{rb}$ are coefficients and I is the intercept, where the coefficients are obtained from solving equation (III) for a set of standard or reference samples with known RON values. It should be recognized that the value of the coefficients will change depending on the points selected.

In another embodiment, the RON is calculated from a more generalized equation (IV):

$$RON = \sum_{i=1,j=1}^{i=m,j=n} c_{ij} ID_i^j + \sum_{k=1,l=1}^{k=m,l=n} c'_{kl} ID_k'^l + I \quad (IV)$$

where $ID_i$ are data points selected from the A region of the profile representing an ignition delay of components in the A region, $ID'_k$ are data points selected from the B region of the profile representing an ignition delay of components in the B region, $c_{ij}$ and $c'_{kl}$ are coefficients and I is the intercept, i is an integer representing a number of data points selected from the A region, j is an integer representing the number of terms in the expansion for the selected data points in the A region, k is an integer representing the number of data points selected from the B region, and l is an integer representing the number of terms in the expansion for the selected data points in the B region, and where the coefficients and intercept are obtained from solving equation (IV) for a set of standard or reference samples. The references or standard sample are a set of samples having well defined RON values (dependent variable), while the ID's (independent variables) are measured. The independent and dependent variables are substituted into the equation and the coefficients are determined using multiple linear regression. In equation (IV), the coefficients of $ID_i$ or $ID_k$ can be set to zero so that the derived RON values are calculated based on a power series expansion about either the $ID_i$ measurements or the $ID_k$ measurements.

In another embodiment, the RON is calculated from a more generalized equation (V):

$$RON = \sum_{i=1,j=1}^{i=m,j=n} c_{ij} ID_i^j + \sum_{k=1,l=1}^{k=o,l=p} c_{kl} ID_k^l + \sum_{\substack{ii=1,jj=1 \\ kk=1}}^{\substack{ii=n,jj=o, \\ kk=m+p}} c_{iijjkk} (ID_{ii}/ID_{jj})^{kk} + I \quad (V)$$

where $ID_i$ are data points selected from the A region of the profile representing an ignition delay of components in the A region, $ID_k$ are data points selected from the B region of the profile representing an ignition delay of components in the B region, and $ID_{ii}/ID_{jj}$ ratios of selected data points from the A region and $ID_{jj}$ are selected points from the B region, $c_{ij}$, $c_{kl}$ and $c_{iijjkk}$ are coefficients and I is the intercept, i is an integer representing a number of data points selected from the A region, j is an integer representing the number of terms in the expansion for the selected data points in the A region, i.e., the power of the term, k is an integer representing the number of data points selected from the B region, l is an integer representing the number of terms in the expansion for the selected data points in the B region, i.e., the power of the terms, ii is an integer representing the number of data points selected from the A region, jj is an integer representing the number of data points selected from the B region, kk is an integer representing the number of terms in the expansion for the ratios of selected data points from region A to selected data points from the B region, i.e., the power of the terms. The coefficients and intercept are obtained from solving equation (V) for a set of standard or reference samples. The references or standard sample are a set of samples having well defined RON values (dependent variable), while the ID's (independent variables) are measured. The independent and dependent variables are substituted into the equation and the coefficients are determined using multiple linear regression. In equation (V), any of the coefficients can be zero, provided at least one term from each summation has non zero coefficients.

In another embodiment, the RON is calculated from an even more generalized equation (VI):

$$RON = \sum_{i=1}^{n} \sum_{j=1,k=1}^{j=m,k=o} c_{ijk} ID_j^k + I \quad (VI)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point raised the kth power and I is the intercept. In Equation VI, i is an integer representing a number of regions, j is an integer representing a number of data points selected from the $i^{th}$ region, j is an integer representing the number of terms in the expansion for the selected data points in expansion, i.e., the power of the term. The coefficients and intercept are obtained from solving equation (VI) for a set of standard or reference samples. The references or standard sample are a set of samples having well defined RON values (dependent variable), while the ID's (independent variables) are measured. The independent and dependent variables are substituted into the equation and the coefficients are determined using multiple linear regression. In equation (VI), the coefficients of all but one of the $ID_j$ can be set to zero so that the derived RON values are calculated based on a power series expansion about a single point in one region of the profile, a single point from two or all of the regions, a single point from one region and a plurality of point from the other regions, a single point from all regions save one and a plurality of points from the one region, or a plurality of points from each region.

In another embodiment, the RON is calculated from an even more generalized equation (VII):

$$RON = \sum_{i=1}^{n} \sum_{j=1,k=1}^{j=m,k=o} c_{ijk} ID_j^k + \sum_{\substack{ii=1,jj=1 \\ kk=1}}^{\substack{ii=m,jj=m, \\ kk=o}} c_{iijjkk} (ID_{ii}/ID_{jj})^{kk} + I \quad (VII)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point of the $i^{th}$ region raised the kb power, $ID_{ii}/ID_{jj}$ are ratios of data points from different regions, $c_{iijjkk}$ are expansion coefficients corresponding to the $ii^{th}$ data point from one region and the $jj^{th}$ data point from a different regions raised to the $kk^{th}$ power and I is the intercept.

In one embodiment, a derived MON is calculated from second order equation (VIII):

$$MON = C_{1a}*ID_1 + C_{2a}*ID_2 + C_{1b}*(ID_1)^2 + C_{2b}*(ID_2)^2 + I \quad (VIII)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$ are coefficients and I is the intercept, where the coefficients obtained from solving equation (I) for a set of standard or reference samples with known MON values. In equation (I), the coefficients of $ID_1$ or $ID_2$ can be set to zero so that the derived MON values are calculated based on a power series expansion about a single ID measurement.

In one embodiment, a derived MON is calculated from second order equation (IX):

$$MON = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \quad (IX)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$, $C_{ra}$, and $C_{rb}$ are coefficients and I is the intercept, where the coefficients are obtained from solving equation (IX) for a set of standard or reference samples with known MON values. In equation (IX), the coefficients of any of the terms can be set to zero so that the derived MON values are calculated based on a power series expansion about a single ID or a single ratio of selected data points. In certain embodiment, the coefficient $C_{rd}$ is set equal to zero. It should be recognized that the value of the coefficients will change depending on the points selected.

In one embodiment, a derived MON is calculated from second order equation (X):

$$MON = C_{ra}ID_1/ID_2 + C_{rb}(ID_1/ID_2)^2 + I \quad (X)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{ra}$ and $C_{rb}$ are coefficients and I is the intercept, where the coefficients are obtained from solving equation (X) for a set of standard or reference samples with known MON values. It should be recognized that the value of the coefficients will change depending on the points selected.

In another embodiment, the MON is calculated from a more generalized equation (XI):

$$MON = \sum_{i=1,j=1}^{i=m,j=n} c_{ij}ID_i^j + \sum_{k=1,l=1}^{k=m,l=n} c_{kl}ID_k^l + I \quad (XI)$$

where $ID_i$ are data points selected from the A region of the profile representing an ignition delay of components in the A region, $ID_k$ are data points selected from the B region of the profile representing an ignition delay of components in the B region, $c_{ij}$ and $c'_{kl}$ are coefficients and I is the intercept, i is an integer representing a number of data points selected from the A region, j is an integer representing the number of terms in the expansion for the selected data points in the A region, k is an integer representing the number of data points selected from the B region, and l is an integer representing the number of terms in the expansion for the selected data points in the B region, and where the coefficients and intercept are obtained from solving equation (XI) for a set of standard or reference samples. The references or standard sample are a set of samples having well defined MON values (dependent variable), while the ID's (independent variables) are measured. The independent and dependent variables are substituted into the equation and the coefficients are determined using multiple linear regression. In equation (XI), the coefficients of $ID_i$ or $ID_k$ can be set to zero so that the derived MON values are calculated based on a power series expansion about either the $ID_i$ measurements or the $ID_k$ measurements.

In another embodiment, the MON is calculated from a more generalized equation (XII):

$$MON = \quad (XII)$$

$$\sum_{i=1,j=1}^{i=m,j=n} c_{ij}ID_i^j + \sum_{k=1,l=1}^{k=o,l=p} c_{kl}ID_k^l + \sum_{\substack{ii=1,jj=1, \\ kk=1}}^{\substack{ii=n,jj=o, \\ kk=m+p}} c_{iijjkk}(ID_{ii}/ID_{jj})^{kk} + I$$

where $ID_i$ are data points selected from the A region of the profile representing an ignition delay of components in the A region, $ID_k$ are data points selected from the B region of the profile representing an ignition delay of components in the B region, and $ID_{ii}/ID_{jj}$ ratios of selected data points from the A region and $ID_{jj}$ are selected points from the B region, $c_{ij}$, $c_{kl}$ and $c_{iijjkk}$ are coefficients and I is the intercept, i is an integer representing a number of data points selected from the A region, j is an integer representing the number of terms in the expansion for the selected data points in the A region, i.e., the power of the term, k is an integer representing the number of data points selected from the B region, l is an integer representing the number of terms in the expansion for the selected data points in the B region, i.e., the power of the terms, ii is an integer representing the number of data points selected from the A region, jj is an integer representing the number of data points selected from the B region, kk is an integer representing the number of terms in the expansion for the ratios of selected data points from region A to selected data points from the B region, i.e., the power of the terms. The coefficients and intercept are obtained from solving equation (XII) for a set of standard or reference samples. The references or standard sample are a set of samples having well defined MON values (dependent variable), while the ID's (independent variables) are measured. The independent and dependent variables are substituted into the equation and the coefficients are determined using multiple linear regression. In equation (XII), any of the coefficients can be zero, provided at least one term from each summation has non zero coefficients.

In another embodiment, the MON is calculated from an even more generalized equation (XIII):

$$MON = \sum_{i=1}^{n} \sum_{j=1,k=1}^{j=m,k=o} c_{ijk} ID_j^k + I \quad (XIII)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point raised the kth power and I is the intercept. In Equation XIII, i is an integer representing a number of regions, j is an integer representing a number of data points selected from the $i^{th}$ region, j is an integer representing the number of terms in the expansion for the selected data points in expansion, i.e., the power of the term. The coefficients and intercept are obtained from solving equation (XIII) for a set of standard or reference samples. The references or standard sample are a set of samples having well defined MON values (dependent variable), while the ID's (independent variables) are measured. The independent and dependent variables are substituted into the equation and the coefficients are determined using multiple linear regression. In equation (XIII), the coefficients of all but one of the $ID_j$ can be set to zero so that the derived MON values are calculated based on a power series expansion about a single point in one region of the profile, a single point from two or all of the regions, a single point from one region and a plurality of point from the other regions, a single point from all regions save one and a plurality of points from the one region, or a plurality of points from each region.

In another embodiment, the MON is calculated from an even more generalized equation (XIV):

$$MON = \sum_{i=1}^{n} \sum_{j=1,k=1}^{j=m,k=o} c_{ijk} ID_j^k + \sum_{\substack{ii=1,jj=1,\\kk=1}}^{\substack{ii=m,jj=m,\\kk=o}} c_{iijjkk} (ID_{ii}/ID_{jj})^{kk} + I \quad (XIV)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point of the $i^{th}$ region raised the $k^{th}$ power, $ID_{ii}/ID_{jj}$ are ratios of data points from different regions, $c_{iijjkk}$ are expansion coefficients corresponding to the $ii^{th}$ data point from one region and the $jj^{th}$ data point from a different regions raised to the $kk^{th}$ power and I is the intercept.

Figure 2:
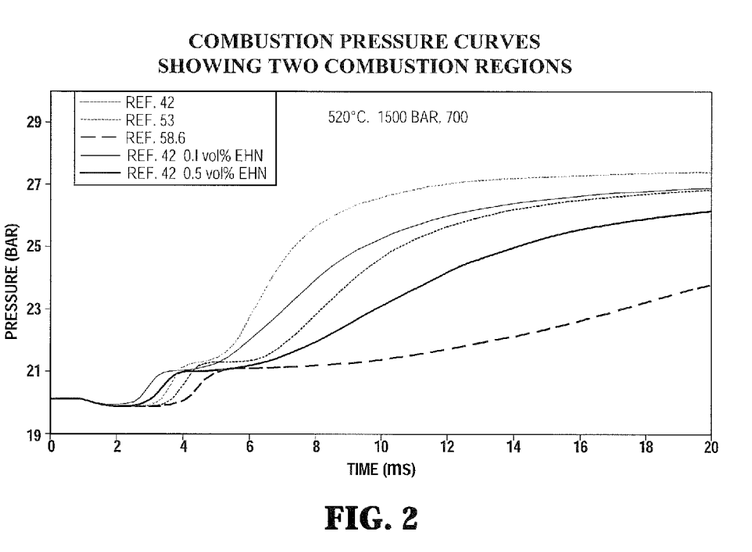
FIG. 2 depicts a plot of samples combusted using the apparatus of FIG. 1 showing two region profiles at 520° C., at 1500 bar, and t=750 ms—for middle distillates showing the type of data curves obtained.

Referring now to FIG. 2, plots of combustion pressure/time profiles for two reference standards and three reference fluids/fuels are shown that were obtained using an apparatus of FIG. 1 at different temperatures, pressures and times for middle distillates are shown to illustrate the type of data produced by an apparatus of FIG. 1 when light distillates are combusted, except that the temperature and pressure values will generally be different. The method utilizes data derived from such plots of combustion pressure/time profiles for two reference standards to calibrate the equations.

The pressure waves or profiles using a modem injector CVCC apparatus typically are different from those obtained using conventional CVCC apparatuses in general use today, which generate profiles typically having only a combustion curve having a single profile or region, i.e., the curve does not show discrimination between early burning components and late burning components. The new CVCC apparatus such as the apparatus of FIG. 1 typically generates profiles having two combustion regions, the A region and the B region. It should be recognized that these regions may not represent separate or distinct curve segments, but one may appear as a shoulder on the other curve segment. Thus, the early burning components may appear as a shoulder on the curve for the late burning components. The present invention requires pressure/time data points from both the early ignition delay region and the later ignition delay region as independent variables in a series expansion equation about these points that yields improved derived RON and/or MON values for lower boiling point hydrocarbon fluids and/or fuels. It should also be recognized that the two or more selected points can be selected so that one represents an early ignition delay and the other represents a late ignition delay so that the power series expansion equation (I) or (II) will have appropriate independent variables for computing derived RON and/or MON values. In certain embodiments, low chamber temperature are used to improve the differentiation between derived RON and/or MON values for samples that would give essentially the derived RON and/or MON value using the conventional ASTM method. The obtained pressure curves or profiles are sensitive to a volume of the injected sample so care must be exercised in sample injection. Additionally, stable stoichiometry (size of sample injected) is important for stable pressure data. The present invention is based on the clear recognition that more than one pressure/time data point (sometimes referred to herein as an ID measurement) along the pressure curve is required to differentiate between hydrocarbon fuels, and biodiesels and to generate derived RON and/or MON values for unknown lower boiling point hydrocarbon fluids/fuels that more closing match what would be their corresponding actual RON and/or MON values. The inventors have found that equations using only a single point ID measurement do not give satisfactory derived RON and/or MON determination for all types of samples. The derived RON and/or MON values obtained from these equations show large and unpredictable derived RON and/or MON value variances relative to their corresponding actual RON and/or MON CN values. The present invention based on at least two point ID measurements, one from each region of the profile, yields derived RON and/or MON values that are better predictors of the corresponding actual RON and/or MON values, i.e., the derived RON and/or MON values are closer to the actual RON and/or MON values.

It should be recognized that the analyzing part of the system of this invention are designed to be coded into a software routine that will run on computer components of the analyzer of the CVCC. Thus, the components of the system and the steps of the method that required computations or calculations are designed to occur in software routines encoding the component or method step. Thus, equations (I-XIV) are designed to be implemented on a computer, where the software in encoded so as to take a set of selected data points from a pressure versus time profile and calculate a derived RON and/or MON value based on a software implementation of one or more of the equations (I-XIV).

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for calculating derived RON and/or MON values comprising the steps of:
    first autoigniting a calibration sample having a known RON and/or MON value in the constant volume combustion chamber apparatus to produce a calibration pressure versus time combustion profile,
    selecting at least one calibration data point from the calibration profile,
    computing a derived RON and/or MON values from a power series expansion equation expanded about the selected calibration data points and/or ratios of the selected calibration data points,
    adjusting expansion coefficients in the equation to minimize a difference between the known RON and/or MON value and the derived RON and/or MON value to obtain a set of optimized expansion coefficients,
    second autoigniting an unknown sample to obtain a pressure versus time combustion profile of said unknown sample using the constant volume combustion chamber apparatus capable of yielding a pressure versus time combustion profile of said unknown sample,
    selecting at least one sample data point from the profile of said unknown sample, and
    calculating a derived RON and/or MON values for said unknown sample from a power series expansion equation expanded about the selected sample data points of said unknown sample and/or ratios of the selected calibration data points using the optimized expansion coefficients;
    wherein the power series expansion equation is selected from the group consisting of the form of equations (I), (II), and (III):

$$RON = C_{1a}*ID_1 + C_{2a}*ID_2 + C_{1b}*(ID_1)^2 + C_{2b}*(ID_2)^2 + I \quad (I)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$ are coefficients and I is the intercept, where the coefficients obtained from solving equation (I) for a set of standard or reference samples with known RON value;

$$RON = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \quad (II)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$, $C_{ra}$, and $C_{rb}$ are coefficients and I is the intercept, where the coefficients are obtained from solving equation (II) for a set of standard or reference samples with known RON values; or $$RON = C_{ra}ID_1/ID_2 + C_{rb}(ID_1/ID_2)^2 + I \quad (III)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{ra}$ and $C_{rb}$ are coefficients and I is the intercept, where the coefficients are obtained from solving equations (III) for a set of standard or reference samples with known RON values.

2. The method of claim 1, wherein the two selecting steps select a single data point from each profile.

3. The method of claim 1, wherein the two selecting steps select at least two data points from each profile.

4. The method of claim 1, wherein the two selecting step selects at least two data points and the two calculating step includes calculating an arithmetic ratio of the data points.

5. The method of claim 1, wherein the two selecting steps select a plurality of data points from each profile.

6. The method of claim 1, wherein each profile has a plurality of regions and the two selecting step selects a single data point from each region.

7. The method of claim 1, wherein each profile has a plurality of regions and the two selecting steps select at a plurality of data points from each region.

8. The method of claim 1, wherein the power series expansion equation terminates with second order terms.

9. A method for calculating derived RON and/or MON values comprising the steps of:
    first autoigniting a calibration sample having a known RON and/or MON value in the constant volume combustion chamber apparatus to produce a calibration pressure versus time combustion profile,
    selecting at least one calibration data point from the calibration profile,
    computing a derived RON and/or MON values from a power series expansion equation expanded about the selected calibration data points and/or ratios of the selected calibration data points,
    adjusting expansion coefficients in the equation to minimize a difference between the known RON and/or MON value and the derived RON and/or MON value to obtain a set of optimized expansion coefficients,
    second autoigniting an unknown sample to obtain a pressure versus time combustion profile of said unknown sample using the constant volume combustion chamber apparatus capable of yielding a pressure versus time combustion profile of said unknown sample,
    selecting at least one sample data point from the profile of said unknown sample, and
    calculating a derived RON and/or MON values for said unknown sample from a power series expansion equation expanded about the selected sample data points of said unknown sample and/or ratios of the selected calibration data points using the optimized expansion coefficients:
    wherein the power series expansion equation is selected from the group consisting of the form of equations (IV), (V), (VI), and (VII);

$$RON = \sum_{i=1,j=1}^{i=m,j=n} c_{ij} ID_i^j + \sum_{k=1,l=1}^{k=m,l=n} c'_{kl} ID_k'^l + I \quad (IV)$$

where $ID_i$ are data points selected from the A region of the profile representing an ignition delay of components in the A region, $ID'_k$ are data points selected from the B region of the profile representing an ignition delay of components in the B region, $c_{ij}$ and $c'_{kl}$ are coefficients and I is the intercept, i is an integer representing a number of data points selected from the A region, j is an integer representing the number of terms in the expansion for the selected data points in the A region, k is an integer representing the number of data points selected from the B region, and l is an integer representing the number of terms in the expansion for the selected data points in the B region, and where the coefficients and intercept are obtained from solving equation (IV) for a set of standard or reference samples;

$$RON = \sum_{i=1,j=1}^{i=m,j=n} c_{ij} ID_i^j + \sum_{k=1,l=1}^{k=o,l=p} c_{kl} ID_k^l + \sum_{\substack{ii=1,jj=1 \\ kk=1}}^{\substack{ii=n,jj=o, \\ kk=m+p}} c_{iijjkk} (ID_{ii}/ID_{jj})^{kk} + I \qquad (V)$$

where $ID_i$ are data points selected from the A region of the profile representing an ignition delay of components in the A region, $ID_k$ are data points selected from the B region of the profile representing an ignition delay of components in the B region, and $ID_{ii}/ID_{jj}$ ratios of selected data points from the A region and $ID_{jj}$ are selected points from the B region, $c_{ij}$, $c_{kl}$ and $c_{iijjkk}$ are coefficients and I is the intercept, i is an integer representing a number of data points selected from the A region, j is an integer representing the number of terms in the expansion for the selected data points in the A region, k is an integer representing the number of data points selected from the B region, l is an integer representing the number of terms in the expansion for the selected data points in the B region, ii is an integer representing the number of data points selected from the A region, jj is an integer representing the number of data points selected from the B region, kk is an integer representing the number of terms in the expansion for the ratios of selected data points from region A to selected data points from the B region;

$$RON = \sum_{i=1}^{n} \sum_{j=1,k=1}^{j=m,k=o} c_{ijk} ID_j^k + I \qquad (VI)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point raised the $k^{th}$ power and I is the intercept, i is an integer representing number of regions, j is an integer representing a number of data points selected from the $i^{th}$ region, k is an integer representing the number of terms in the expansion for the selected data points in expansion; or $$RON = \sum_{i=1}^{n} \sum_{j=1,k=1}^{j=m,k=o} c_{ijk} ID_j^k + \sum_{\substack{ii=1,jj=1 \\ kk=1}}^{\substack{ii=m,jj=m, \\ kk=o}} c_{iijjkk} (ID_{ii}/ID_{jj})^{kk} + I \qquad (VII)$$

where $ID_j$ are data points selected from the $i^{th}$ region of the profile, where each region represents components having different ignition delay time and $c_{ijk}$ are expansion coefficients corresponding to the $i^{th}$ region, the $i^{th}$ point of the $i^{th}$ region raised the $k^{th}$ power, $ID_{ii}/ID_{jj}$ are ratios of data points from different regions, $c_{iijjkk}$ are expansion coefficients corresponding to the $ii^{th}$ data point from one region and the $jj^{th}$ data point from a different region raised to the $kk^{th}$ power and I is the intercept.

10. A method for calculating derived RON and/or MON values comprising the steps of:
first autoigniting a calibration sample having a known RON and/or MON value in the constant volume combustion chamber apparatus to produce a calibration pressure versus time combustion profile,
selecting at least one calibration data point from the calibration profile,
computing a derived RON and/or MON values from a power series expansion equation expanded about the selected calibration data points and/or ratios of the selected calibration data points,
adjusting expansion coefficients in the equation to minimize a difference between the known RON and/or MON value and the derived RON and/or MON value to obtain a set of optimized expansion coefficients,
second autoigniting an unknown sample to obtain a pressure versus time combustion profile of said unknown sample using the constant volume combustion chamber apparatus capable of yielding a pressure versus time combustion profile of said unknown sample,
selecting at least one sample data point from the profile of said unknown sample, and
calculating a derived RON and/or MON values for said unknown sample from a power series expansion equation expanded about the selected sample data points of said unknown sample and/or ratios of the selected calibration data points using the optimized expansion coefficients;
wherein the power series expansion equation is selected from the group consisting of the form of equations (VIII), (IX), and (X);

$$MON = C_{1a}*ID_1 + C_{2a}*ID_2 + C_{1b}*(ID_1)^2 + C_{2b}*(ID_2)^2 + I \qquad (VIII)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$ are coefficients and I is the intercept;

$$MON = C_{1a}ID_1 + C_{2a}ID_2 + C_{1b}(ID_1)^2 + C_{2b}(ID_2)^2 + C_{ra}ID_1/ID_2 + C_{rb}(ID_1/ID_2)^2 + I \qquad (IX)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{1a}$, $C_{1b}$, $C_{2a}$, $C_{2b}$, $C_{ra}$ and $C_{rb}$ are coefficients and I is the intercept, where the coefficients are obtained from solving equation (IX) for a set of standard or reference samples with known MON values; or $$MON = C_{ra}ID_1/ID_2 + C_{rb}(ID_1/ID_2)^2 + I \qquad (X)$$

where $ID_1$ is a data point selected from the A region of the pressure/time profile representing an ignition delay of components in the A region, $ID_2$ is a data point selected from the B region of the pressure/time profile representing an ignition delay of components in the B region, $C_{ra}$ and $C_{rb}$ are coefficients and I is the intercept, where the coefficients are obtained from solving equation (X) for a set of standard or reference samples with known MON values.

11. A method for calculating derived RON and/or MON values comprising the steps of:
first autoigniting a calibration sample having a known RON and/or MON value in the constant volume combustion chamber apparatus to produce a calibration pressure versus time combustion profile, selecting at least one calibration data point from the calibration profile, computing a derived RON and/or MON values from a power series expansion equation expanded about the selected calibration data points and/or ratios of the selected calibration data points, adjusting expansion coefficients in the equation to minimize a difference between the known RON and/or MON value and the derived RON and/or MON value to obtain a set of optimized expansion coefficients, second autoigniting an unknown sample to obtain a pressure versus time combustion profile of said unknown sample using the constant volume combustion chamber apparatus capable of yielding a pressure versus time combustion profile of said unknown sample, selecting at least one sample data point from the profile of said unknown sample, and calculating a derived RON and/or MON values for said unknown sample from a power series expansion equation expanded about the selected sample data points of said unknown sample and/or ratios of the selected calibration data points using the optimized expansion coefficients;

wherein the power series expansion equation is selected from the group consisting of the form of equations (XI), (XII), (XIII), and (XIV);

$$MON = \sum_{i=1, j=1}^{i=m, j=n} c_{ij} ID_i^j + \sum_{k=1, l=1}^{k=m, l=n} c_{kl} ID_k^l + I \quad (XI)$$

where $ID_i$ are data points selected from the A region of the profile representing an ignition delay of components in the A region, $ID_k$ are data points selected from the B region of the profile representing an ignition delay of components in the B region, $c_{ij}$ and $c'_{kl}$ are coefficients and I is the intercept, i is an integer representing a number of data points selected from the A region, j is an integer representing the number of terms in the expansion for the selected data points in the A region, k is an integer representing the number of data points selected from the B region, and l is an integer representing the number of terms in the expansion for the selected data points in the B region, and where the coefficients and intercept are obtained from solving equation (XI) for a set of standard or reference samples;

$$MON = \sum_{i=1,j=1}^{i=m,j=n} c_{ij} ID_i^j + \sum_{k=1,l=1}^{k=o,l=p} c_{kl} ID_k^l + \sum_{\substack{ii=1,jj=1,\\kk=1}}^{\substack{ii=n,jj=o,\\kk=m+p}} c_{iijjkk} (ID_{ii}/ID_{jj})^{kk} + I \quad (XII)$$

where $ID_i$ are data points selected from the A region of the profile representing an ignition delay of components in the A region, $ID_k$ are data points selected from the B region of the profile representing an ignition delay of components in the B region, and $ID_{ii}/ID_{jj}$ ratios of selected data points from the A region and $ID_{jj}$ are selected points from the B region, $c_{ij}$, $c_{kl}$, $c_{iijjkk}$ are coefficients and I is the intercept, i is an integer representing a number of data points selected from the A region, j is an integer representing the number of terms in the expansion for the selected data points in the A region, k is an integer representing the number of data points selected from the B region, l is an integer representing the number of terms in the expansion for the selected data points in the B region, ii is an integer representing the number of data points selected from the A region, jj is an integer representing the number of data points selected from the B region, kk is an integer representing the number of terms in the expansion for the ratios of selected data points from region A to selected data points from the B region;

$$MON = \sum_{i=1}^{n} \sum_{j=1,k=1}^{j=m,k=o} c_{ijk} ID_j^k + I \quad (XIII)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point raised the $k^{th}$ power and I is the intercept, i is an integer representing a number of regions, j is an integer representing a number of data points selected from the $i^{th}$ region, k is an integer representing the number of terms in the expansion for the selected data points in expansion, and coefficients and intercept are obtained from solving equation (XIII) for a set of standard or reference samples; or $$MON = \sum_{i=1}^{n} \sum_{j=1,k=1}^{j=m,k=o} c_{ijk} ID_j^k + \sum_{\substack{ii=1,jj=1,\\kk=1}}^{\substack{ii=m,jj=m,\\kk=o}} c_{iijjkk} (ID_{ii}/ID_{jj})^{kk} + I \quad (XIV)$$

where $ID_j$ are data points selected from the $i^{th}$ region of the profile, where each region represents components having different ignition delay time and $c_{ijk}$ are expansion coefficients corresponding to the $i^{th}$ region, the $j^{th}$ point of the $i^{th}$ region raised the $k^{th}$ power, $ID_{ii}/ID_{jj}$ are ratios of data points from different regions, $c_{iijjkk}$ are expansion coefficients corresponding to the $ii^{th}$ data point from one region and the $jj^{th}$ data point from a different region raised to the $kk^{th}$ power and I is the intercept.

* * * * *